United States Patent [19]
Afflerbach

[11] Patent Number: 5,265,605
[45] Date of Patent: Nov. 30, 1993

[54] WOUND ASSESSMENT METHOD AND APPARATUS

[76] Inventor: Denise E. Afflerbach, 202 Stirrup, Victoria, Tex. 77901

[21] Appl. No.: 904,376

[22] Filed: Jun. 25, 1992

[51] Int. Cl.$^5$ ............................................. A61B 5/107
[52] U.S. Cl. ...................................... 128/630; 602/42
[58] Field of Search ............... 128/630, 773, 897, 898; 602/41–46, 52–58

[56] References Cited
U.S. PATENT DOCUMENTS 5,000,172  3/1991  Ward ..................................... 602/57

*Primary Examiner*—Lee S. Cohen
*Assistant Examiner*—Marianne Parker
*Attorney, Agent, or Firm*—Donald R. Comuzzi

[57] ABSTRACT

The present invention is a wound assessment tool comprising a wound assessment sheet, having a place for writing wound assessment parameters and a wound assessment graph for tracing wound margins printed thereon, peelably secured to a disposable transparent flexible backing sheet. The backing sheet serves to prevent the wound assessment sheet from contacting the wound. Thus, after the wound is documented, the wound assessment sheet may be removed from the backing sheet which is then disposed. The wound assessment sheet is then secured to a wound assessment worksheet using an adhesive material on the back of the wound assessment sheet which originally secured the wound assessment sheet to the sterile backing sheet, thereby, creating a permanent record of the patient's wound.

3 Claims, 2 Drawing Sheets

WOUND ASSESSMENT METHOD AND APPARATUS

BACKGROUND OF THE INVENTION

The present invention relates to a method and apparatus for wound assessment. The first and most basic step in wound care is an assessment and documentation of the wound to ascertain its characteristics which then allows an informed decision to be made concerning treatment. Wound characteristics which must be assessed include not only wound dimension (i.e. size and shape) measurements but also location, depth, staging, color, presence of eschar, erythema, odor, drainage, and presence of undermining.

Wound measuring devices presently available consist of variable size flexible or stiff plastic sheets employed in a ruler-like fashion to measure a wound's dimensions. The device is placed over top of the wound so that the wound's dimensional information may be measured and recorded, either by memory or scratch notes for later transcription onto a permanent document. The wound measuring device is then disposed. Disposable plastic measuring devices are inefficient because they waste time, are inaccurate, and permit valuable wound data to be discarded. They waste time because the original data must later be transferred to a permanent patient chart, with such a transference also creating inaccuracies which result from the erroneous entrance of the original data onto the permanent patient record. Additionally, any wound sketch made on the disposable plastic measuring device will be lost with the disposal of the device. Thus, a wound sketch which may be extremely useful in later wound examinations has been lost. Disposable plastic measuring devices, therefore, do not present a practical solution to the problem of wound assessment.

A second type of wound assessment device is the "Flexigrid" marketed by Smith and Nephew. That device consists of a peel away top grid placed over an Opsite dressing. Unfortunately, Opsite is not always needed, practical, or the proper dressing for a wound. In such instances, the "Flexigrid" cannot be used.

Thus, the present invention has been developed to be a non-disposable wound assessment tool usable in any and all wound situations.

SUMMARY OF THE INVENTION

The present invention comprises a backing sheet and a wound assessment sheet made of any suitable transparent flexible material such as plastic. The back of the wound assessment sheet is coated with an adhesive material such as glue so that it peelably attaches to the front of the backing sheet. Printed on the wound assessment sheet are all the required parameters for documenting a wound such as dimensional measurements, location, depth, staging, color, presence of eschar, erythema, odor, drainage, and presence of undermining. Additionally, the wound assessment sheet contains a wound assessment graph printed thereon. The wound assessment graph allows a wound assessor to accurately trace the outline of the wound. Additionally, because the wound assessment graph is provided with a measurement system, an accurate measurement of the wound's dimensions may easily be obtained.

In use, the above parameters are measured and then recorded on the wound assessment sheet using a permanent marker or a grease pencil. The backing sheet, which must be clean, and the attached wound assessment sheet are then placed directly over the wound so that an accurate wound sketch may be made on the wound graph. Next, the wound assessment sheet is separated from the backing sheet, and the backing sheet which has been in contact with the wound is disposed. The adhesive material on the back of the wound assessment sheet serves to initially secure the wound assessment sheet to the backing sheet and, further, serves to secure the wound assessment sheet to a wound assessment worksheet which is then placed in the patient's medical file for later reference.

Thus, it is an object of the present invention to provide a wound assessment tool capable of fully assessing a wound immediately at the time of viewing.

It is a further object of the present invention to provide a wound assessment tool onto which wound documentation parameters may be directly recorded using a color coding system.

It is another object of the present invention to provide a wound assessment tool which is constructed of material flexible enough to conform a wound's shape regardless of location on the patient, but still rigid enough to form a permanent record in a patient's chart.

It still is another object of the present invention to provide a wound assessment tool onto which the wounds margins and dimensions may be traced.

It is still a further object of the present invention to provide a wound assessment tool which speeds up the wound assessment process by eliminating the need of transferring assessment data to another sheet.

It is even another object of the present invention to provide a wound assessment tool which improves measurement accuracy by providing a virtually self explanatory measuring tool.

It is still another object of the present invention to provide a non-disposable wound assessment tool which allows a visual comparison of a sketch of the wound to be made from week-to-week instead of just comparing wound numbers.

It is still a further object of the present invention to develop a wound assessment tool capable of being used to size the stomas of ostomy patients.

It is still an additional object of the present invention to develop a wound assessment tool capable of providing consistent and accurate measurements of dermal ulcers.

Still other features and advantages of the present invention will become evident to those skilled in the art in light of the following.

DETAILED DESCRIPTION OF THE PREFERRED EMBODIMENT

Figure 1:
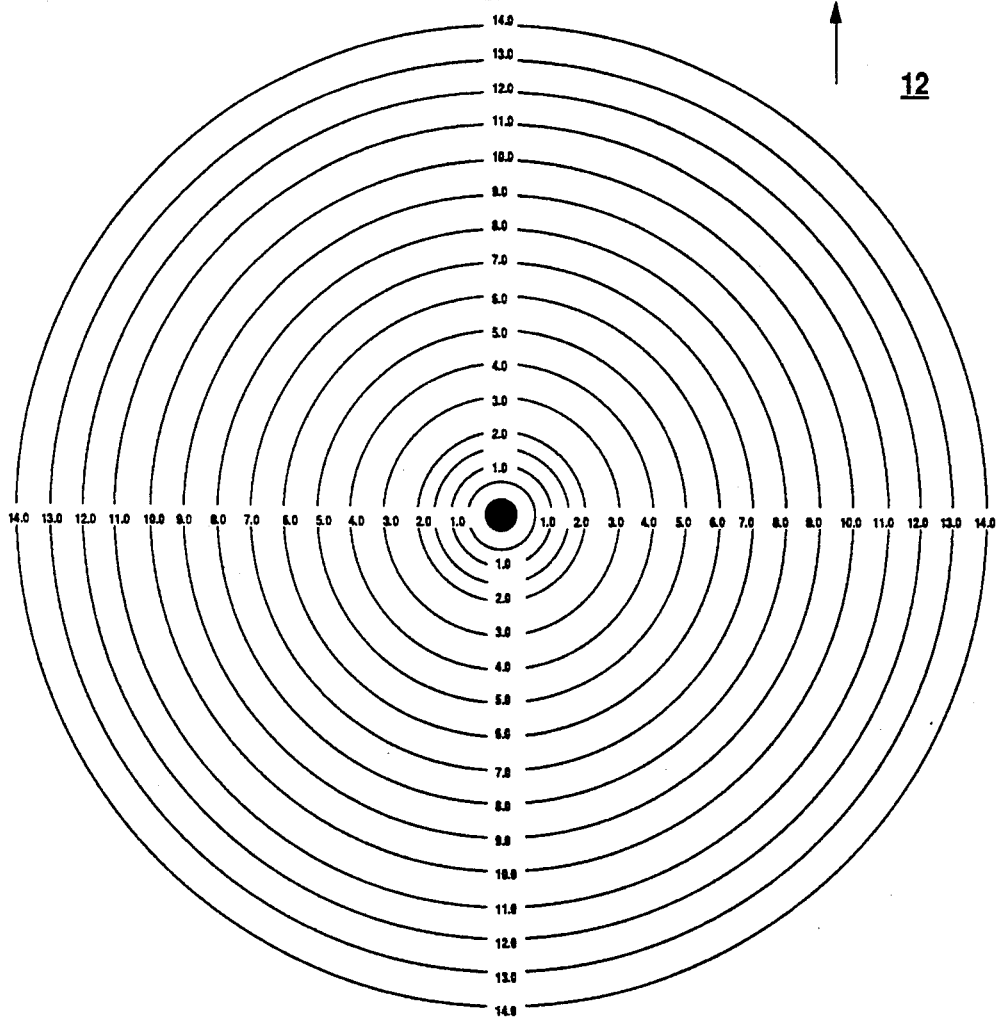
FIG. 1 is a front view of the wound assessment tool according to the preferred embodiment of the present invention showing the transparent disposable backing sheet and the wound assessment sheet.
Figure 4:
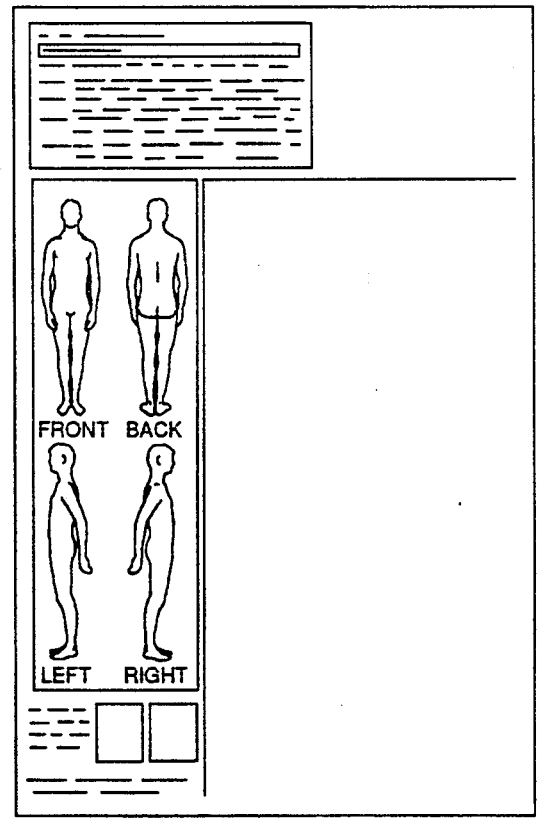
FIG. 4 shows the wound assessment worksheet according to the preferred embodiment of the present invention.

Referring to FIG. 1, the wound assessment tool according to the preferred embodiment of the present invention will be described. Wound assessment tool 10 comprises backing sheet 11 and wound assessment sheet 12 which are both constructed of a flexible transparent material such as plastic. Wound assessment sheet 12 further has the required parameters for documenting a wound (i.e. dimensional measurements, location, depth, staging, color, presence of eschar, erythema, odor, drainage, and presence of undermining) and a wound assessment graph consisting of concentric circles spaced one centimeter apart printed on its front. The back of wound assessment sheet 12 is coated with an adhesive material such as glue which allows it to remain tacked to backing sheet 11 until manually removed. The adhesive material placed on the back of wound assessment sheet 12 further serves to secure wound assessment sheet 12 to the wound assessment worksheet shown in FIG. 4 after a wound has been documented.

Figure 2:
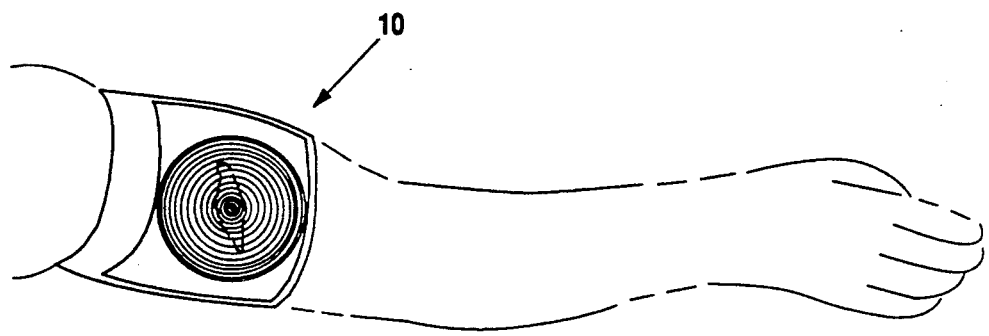
FIG. 2 shows the wound assessment tool according to the preferred embodiment of the present invention placed over a patient's wound for wound tracing.
Figure 3:
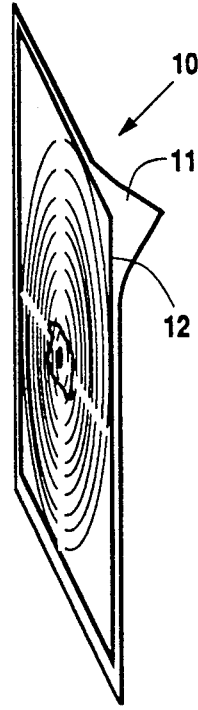
FIG. 3 is a perspective view of the wound assessment tool according to the preferred embodiment of the present invention showing the wound assessment sheet being peelably removed from the transparent disposable backing sheet.

To document a wound, the wound is first visually inspected and the particular wound parameters are determined. Once ascertained, the particular wound parameters are entered onto the wound parameter portion of wound assessment sheet 12 using a permanent magic marker. Wound assessment tool 10 is then placed over top of the wound with backing sheet 11, which must be clean, contacting the wound as shown in FIG. 2. The center of the wound assessment graph printed on wound assessment sheet 12 is placed at the center of the wound with the position arrow pointing at the patient's head. Once wound assessment tool 10 is in place, the wound assessor traces the wound using a permanent marker. The wound may be documented as follows: the wound margins are traced with a blue marker, the eschar is traced with a black marker, and the erythema is traced with a red marker. After the tracing dries, wound assessment sheet 12 is peeled from backing sheet 11 as shown in FIG. 3, and backing sheet 11 is then disposed. Next, wound assessment sheet 12 is placed onto the wound assessment worksheet shown in FIG. 4 and secured using the adhesive material on the back of wound assessment sheet 12. Thus, a complete documentation of a patient's wound may be created for later reference if necessary.

Although the present invention has been described in conjunction with the foregoing specific embodiment, other alternatives, variations, and modifications will be apparent to those of ordinary skill in the art. Those alternatives, variations, and modifications are intended to fall within the spirit and scope of the appended claims.

I claim:

1. A method for assessing and documenting a wound using a wound assessment and documentation apparatus comprising a wound assessment sheet, having wound documentation parameters and a wound assessment graph printed thereon, adhesively secured and peelably removable from a flexible disposable transparent backing sheet, comprising:

visually inspecting said wound and measuring said wound documentation parameters;

entering said wound documentation parameters onto said wound assessment sheet;

placing said wound assessment and documentation apparatus onto said wound with said backing sheet contacting said wound;

tracing the outline of said wound onto said wound assessment graph;

separating said wound assessment sheet from said backing sheet;

disposing of said backing sheet.

2. The method according to claim 1, further comprising the step of placing said wound assessment sheet onto a wound assessment worksheet to create a permanent record of said wound.

3. The method according to claim 1, wherein the step of placing said wound assessment and documentation apparatus onto said wound further includes the step of centering said wound assessment graph on the center of said wound with a position arrow printed on said wound assessment graph pointing towards a patient's head.

* * * * *